US005470342A

United States Patent [19]
Mann et al.

[11] Patent Number: 5,470,342
[45] Date of Patent: Nov. 28, 1995

[54] ADAPTIVE REFRACTORY PERIOD WITHIN IMPLANTABLE CARDIOVERTER-DEFIBRILLATOR

[75] Inventors: Brian M. Mann, Beverly Hills; James D. Causey, III, Simi Valley, both of Calif.

[73] Assignee: Pacesetter, Inc., Sylmar, Calif.

[21] Appl. No.: 226,787

[22] Filed: Apr. 12, 1994

[51] Int. Cl.$^6$ .................................................. A61N 1/39
[52] U.S. Cl. ........................... 607/5; 607/13; 607/4
[58] Field of Search ............................ 607/9, 13, 28, 607/5, 4; 128/696

[56] References Cited

U.S. PATENT DOCUMENTS

| | | | |
|---|---|---|---|
| 4,708,142 | 11/1987 | DeCote | 128/419 |
| 4,708,144 | 11/1987 | Hamilton et al. | 128/419 |
| 4,712,555 | 12/1987 | Thornander et al. | 128/419 |
| 4,774,952 | 10/1988 | Smits | 128/419 |
| 4,809,697 | 3/1989 | Causey et al. | 128/419 |
| 4,817,605 | 4/1989 | Sholder | 128/419 |
| 4,944,299 | 7/1990 | Silvian | 128/419 |
| 4,989,602 | 2/1991 | Sholder et al. | 128/419 |
| 4,998,975 | 3/1991 | Cohen et al. | 128/419 |
| 5,040,534 | 8/1991 | Mann et al. | 128/419 |
| 5,103,820 | 4/1992 | Markowitz | 607/9 |
| 5,103,822 | 4/1992 | Duncan | 128/419 |
| 5,330,504 | 7/1994 | Somerville et al. | 607/5 |
| 5,395,393 | 3/1995 | Wickham | 607/5 |

OTHER PUBLICATIONS

Luceri, et al., *PACE*, vol. 14, pp. 1870–1874 (Nov. 1991).
Cannom, *PACE*, vol. 15, pp. 1–5 (Jan. 1992).

*Primary Examiner*—William E. Kamm
*Assistant Examiner*—Kennedy J. Schaetzle
*Attorney, Agent, or Firm*—Malcolm J. Romano

[57] ABSTRACT

An implantable cardioverter-defibrillator (ICD) adaptively adjusts the refractory period and sensitivity setting of its sensing channel in order to optimally detect depolarization signals indicative of intrinsic cardiac rhythm or tachycardias, or depolarization signals indicative of fibrillation. In one embodiment, the ICD utilizes first and second depolarization signal processing channels, each having first and second refractory periods and first and second sensitivity settings, respectively. The sensitivity settings of the first processing channel are adaptively adjusted to sense normal depolarization signals and tachycardias. The sensitivity settings of the second processing channel are adaptively adjusted to sense fibrillation. Both the first and second refractory periods begin following either a paced depolarization or a sensed depolarization.

22 Claims, 6 Drawing Sheets

ADAPTIVE REFRACTORY PERIOD WITHIN IMPLANTABLE CARDIOVERTER-DEFIBRILLATOR

FIELD OF THE INVENTION

The present invention relates to implantable medical devices and methods, and more particularly to an implantable cardioverter-defibrillator (ICD) that utilizes an adaptive refractory period in order to optimally sense different types of depolarization signals.

BACKGROUND OF THE INVENTION

A depolarization signal (a small electrical impulse) is generated by most mammalian muscle tissue as such tissue contracts. Thus, the beating or contracting of a human heart is manifest by appropriate depolarization signals evidencing the contraction of the atria, referred to as the P-wave, and the contraction of the ventricles, referred to as the R-wave (or the QRS complex). The sequence of P-waves followed by R-waves thus comprises an electrogram or electrocardiogram signal that can be monitored by appropriate electrical circuits to indicate the status of the heart.

An implantable pacemaker includes sensing circuits that monitor the heart by looking for the occurrence of P-waves and/or R-waves, and pacing circuits that stimulate the heart with an appropriate electrical stimulation pulse in the event that a depolarization signal is not sensed within a prescribed time period. In this way, if the heart does not beat naturally within the prescribed time period, i.e., if the heart does not beat on its own so as to maintain a minimum heart rate as defined by the prescribed time period, then an electrical stimulation pulse is provided to force the heart muscle tissue to contract, thereby assuring that the prescribed minimum heart rate is maintained.

An implantable cardioverter-defibrillator (ICD) typically includes sensing and pacing circuits to provide electrical stimulation pulses aimed at responding to slow intrinsic (natural) cardiac rates or asystole (a non-beating heart). The pacing circuits may also provide appropriate electrical stimulation pulses, typically in a prescribed burst or pattern, aimed at terminating rapid intrinsic rates (tachyarrhythmias or tachycardias).

It is common in implantable devices such as pacemakers and ICD's to employ "refractory periods" during those time periods when the sensing circuits of the implantable device are inhibited or otherwise rendered ineffective. Refractory periods are necessary in an implantable device to prevent "over sensing," a phenomena wherein a natural or other event associated with a depolarization, such as the repolarization of cardiac tissue referred to as a T-wave, or an afterpotential remaining after a paced depolarization, is sensed and incorrectly assumed to be a natural depolarization. Thus, the refractory period defines a period of time immediately following a natural or paced depolarization during which all such natural or other events are blocked out and prevented from being sensed.

An ICD must sense intrinsic cardiac activity over a broad dynamic range. That is, cardiac activity ranging from very low amplitude ventricular fibrillation signals (evidenced by rapid depolarization signals having a magnitude of about 1 mV pk-pk or less), to higher amplitude ventricular tachycardia signals (evidenced by depolarization signals having a magnitude of up to 10 mV pk-pk), to normal ventricular and/or atrial depolarization signals (associated with slower intrinsic heart beats and also having a magnitude that may vary up to 10 mV pk-pk or higher), must all be sensed. Such sensing is made difficult because the sensitivity of the sensing circuits needed to sense one type of depolarization signal is not the same as is needed to sense another type of depolarization signal. Moreover, the relatively short refractory period needed to permit sensing very high rate tachyarrhythmias may be too short to effectively block or inhibit the sensing of afterpotentials or repolarizations or other commonly present signals associated with normal cardiac activity, evoked responses, or fibrillation. What is needed, therefore, is an ICD wherein both the sensitivity of the sensing circuits and the duration of the refractory period are automatically adjusted to optimal values depending upon the type of sensing function being carried out.

SUMMARY OF THE INVENTION

The present invention advantageously addresses the above and other needs by providing an implantable cardioverter-defibrillator (ICD) that automatically adapts its refractory period and sensitivity setting to best detect a variety of cardiac events, even though such cardiac events may have conflicting detection criteria. Thus, for example, when looking for the occurrence of normal depolarizations or tachycardias, the refractory period is adaptively set to a first value, and the sensitivity of the sensing circuits is adaptively set to optimally sense the relatively higher amplitude depolarization signals associated with such normal depolarizations or tachycardias. When looking for the occurrence of fibrillation, on the other hand, the refractory period is adaptively set to a second value, and the sensitivity of the sensing circuits is adaptively set to optimally sense the relatively low amplitude depolarization signals typically associated with fibrillation.

In one embodiment, an ICD made in accordance with the invention utilizes two parallel signal processing channels. Each signal processing channel has a respective refractory period associated therewith. The refractory period in both channels follows either a paced depolarization or a sensed depolarization.

A first of the two sensing channels of such embodiment senses normal depolarizations and tachycardias and has a first refractory period. During the first refractory period, sensing is inhibited in the first sensing channel to prevent the sensing of the afterpotential or the repolarization (T-wave) from being misinterpreted as an R-wave. Immediately after the first refractory period, sensing in the first sensing channel is re-enabled and the sensitivity of the first channel, i.e., its sensing threshold and/or gain, is optimized for the function of sensing normal depolarizations or monomorphic tachycardias.

A second of the two sensing channels of the above-described embodiment senses fibrillation and has a second refractory period. During the second refractory period, which is typically shorter than the first refractory period (but may be longer), sensing is inhibited to prevent falsely identifying the paced event afterpotential as a second intrinsic depolarization. Immediately after the second refractory period, sensing in the second sensing channel is re-enabled and the sensitivity of the second channel (sensing threshold and/or gain) is optimized for the function of sensing fibrillation.

In accordance with one aspect of the invention, the sensitivity of the sensing circuits of an ICD is adjusted by changing the threshold setting above which a monitored signal must rise before it is sensed and/or by adjusting the gain of the sensing amplifier used to sense the monitored signal. Thus, for example, in the event normal depolarizations or tachycardias are to be sensed (typically manifest by a depolarization signal having a magnitude on the order of, e.g., 10 mV pk-pk), the threshold setting of the sensing circuit may be set at a high value and/or the gain of the sensing circuit may be decreased. In the event fibrillation is to be sensed (typically manifest by a rapid or chaotic frequency depolarization signal having a magnitude on the order of, e.g., 1 mV pk-pk), the threshold setting of the sensing circuit may be set at a low value and/or the gain of the sensing circuit may be increased.

In accordance with another embodiment of the invention, the refractory period of an ICD is divided into phases or segments, with different sensing options being activated at the conclusion of each phase or segment to optimally sense desired cardiac activity that occurs at the conclusion of each phase or segment.

It is a feature of the present invention to provide an ICD that utilizes two independently programmable refractory periods, a first refractory period being used when sensing normal depolarizations and tachycardias, and a second refractory period being used when sensing fibrillation. In a typical application, it is a feature of the invention, for example, to utilize a longer refractory period when sensing fibrillation than when sensing normal depolarization and tachycardias.

It is another feature of the invention to provide such an ICD that adaptively adjusts the refractory periods, gain and/or threshold settings of the signal processing channels to optimally sense different types of depolarization signals, e.g., the relatively high magnitude depolarization signals associated with normal cardiac depolarizations and tachycardias, or the relatively low magnitude depolarization signals associated with fibrillation.

It is a further feature of the invention to provide an ICD having two parallel signal processing channels for sensing depolarization signals sensed over a single sensing lead (or lead network), each processing channel having its own independently programmable refractory period, and each signal processing channel further having its own independently adjustable gain and/or threshold setting.

It is an additional feature of the invention to provide such an ICD wherein the respective refractory periods, and/or gain/threshold settings of the respective processing channels, are adaptively adjusted to optimally sense: (1) normal cardiac depolarizations, whether associated with natural cardiac rhythm or tachyarrhythmias; or (2) fibrillation.

BRIEF DESCRIPTION OF THE DRAWINGS

The above and other aspects, features and advantages of the present invention will be more apparent from the following more particular description thereof, presented in conjunction with the following drawings wherein:

FIGS. 8-1 and 8-2 show a simplified flow chart that illustrates the process carried out by the control and decision logic of the ICD of FIG. 4 as the ICD carries out its function of detecting tachycardias or fibrillation and applying appropriate therapy.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
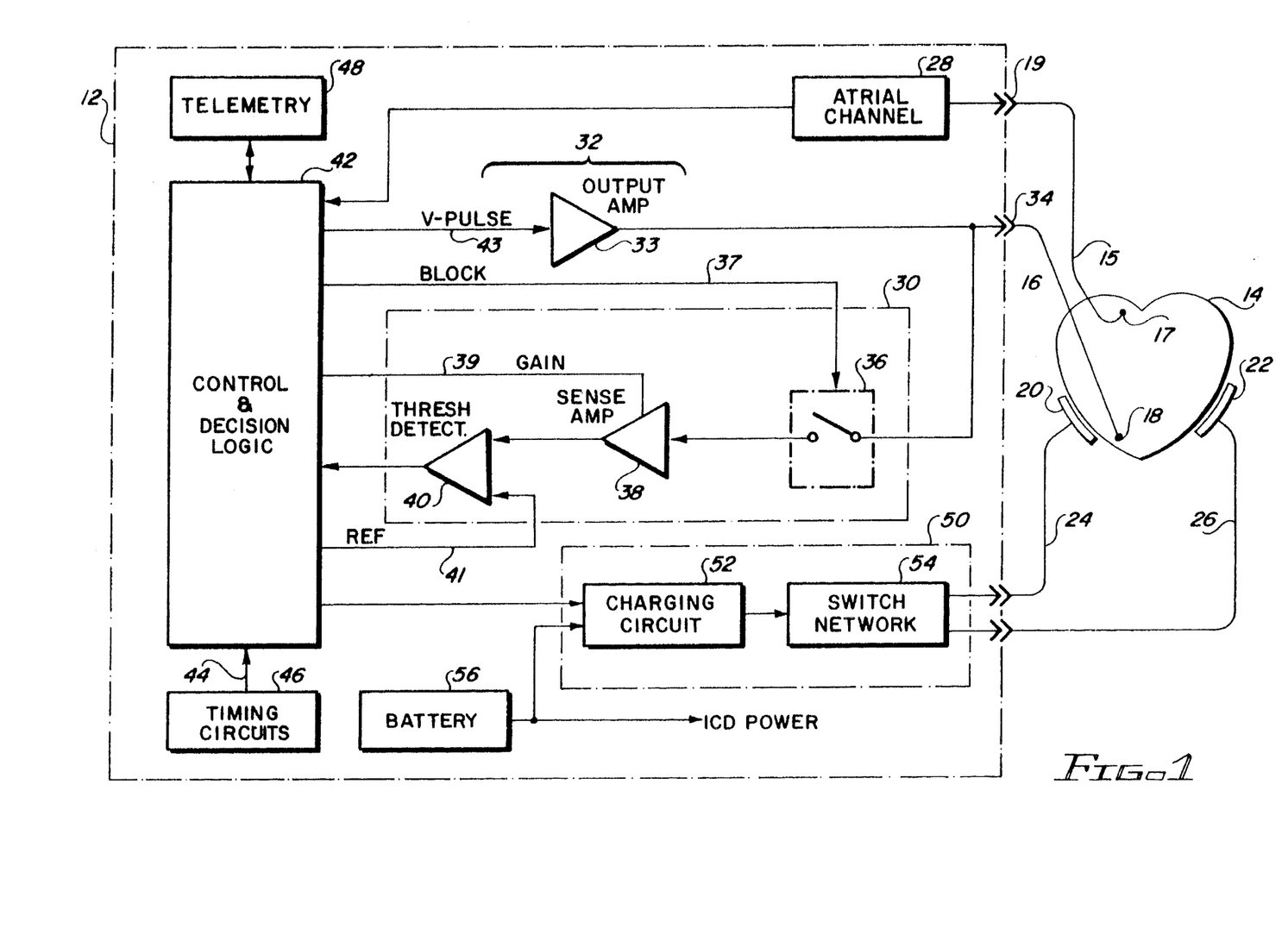
FIG. 1 shows a functional block diagram of an implantable cardioverter-defibrillator (ICD) made in accordance with one embodiment of the invention.

Referring first to FIG. 1, there is shown a block diagram of one embodiment of an ICD 12 made in accordance with the present invention. As shown in FIG. 1, the ICD 12 is electrically connected to a heart 14 by means of at least one sensing/pacing lead 16. Typically, the lead 16 is an endocardial lead designed to be inserted inside of the heart, and having at least one electrode 18 adapted to interface with cardiac tissue. For some applications, it may be desirable to use more than one sensing/pacing lead, or to use a lead having more than one electrode, as is known in the pacing art. Thus, an additional sensing/pacing lead 15 having an electrode 17 is also shown in FIG. 1. As depicted in FIG. 1, the electrode 17 (and corresponding sensing/pacing lead 15) interfaces with cardiac tissue in the atrium of the heart 14, and the electrode 18 (and corresponding sensing/pacing lead 16) interfaces with cardiac tissue in the ventricle of the heart. It is through the sensing/pacing leads 15 and 16 that the depolarization signal, e.g., P-wave or R-wave (or QRS complex), of the heart is sensed. The depolarization signal, as is known in the art, occurs as the heart muscle tissue contracts. The actual physical contraction of the heart immediately follows the depolarization signal. It is also through the sensing/pacing leads 15 and 16 that electrical stimulation pulses of nominal energy are delivered to the heart in order to force a depolarization.

The electrical circuits within the pacemaker 12 that interface with the sensing/pacing lead 16 are generally referred to as the "ventricular channel" (because the sensing and pacing that occurs through the corresponding electrode 18 occurs within the ventricle of the heart). Similarly, the electrical circuits within the pacemaker 12 that interface with the sensing/pacing lead 15 are referred to as the "atrial channel" (because the sensing and pacing that occurs through the corresponding electrode 17 occurs within the atrium of the heart). Each channel, both ventricular and atrial, includes appropriate circuits for both pacing and sensing. For purposes of the present application, only the ventricular channel is described in detail; but it is to be understood that the atrial channel, shown as a single block 28 in FIG. 1, includes the same basic circuitry as the ventricular channel.

As further seen in FIG. 1, two defibrillation electrodes 20 and 22 are likewise electrically coupled to the heart 14 by way of defibrillation leads 24 and 26, respectively. Such defibrillation electrodes are typically utilized in a bipolar configuration, with one electrode being charged positive and the other negative, thereby allowing the largest possible voltage potential to be developed across the heart. It is to be understood that while the defibrillation leads and electrodes depicted in FIG. 1 are shown as epicardial leads and electrodes, such is only exemplary, as endocardial defibrillation leads and electrodes may also be used, as may any type of lead/electrode configuration that allows a high energy electrical shock to be delivered to the heart.

The ventricular channel of the ICD 12 shown in FIG. 1 includes a sensing channel 30 and a pacing channel 32 detachably coupled to the sensing/pacing lead 16 through an appropriate connector 34. (Similarly, the atrial channel 28 includes both a sensing channel and a pacing channel detachably coupled to the sensing/pacing lead 15 through an appropriate connector 19. However, the pacing and sensing channels of the atrial channel 28 will not be described herein as they are substantially the same as those of the ventricular channel.) Both the sensing channel 30 and the pacing channel 32 are controlled and/or monitored by control and decision logic 42. The sensing channel 30 senses electrical signals present at the electrode 18 of the sensing pacing lead 16. If the electrical signals are sufficiently large, they are interpreted as depolarization signals, e.g., an R-wave, evidencing a natural contraction of the heart 14. If the electrical signals are too small, or if no electrical signals occur, then the absence of a sensed depolarization signal may be interpreted by the control and decision logic 42 as a failure of the heart to beat on its own, whereupon an electrical stimulation pulse may be delivered to the heart by way of the pacing channel 32.

As seen in FIG. 1, the pacing channel 32 includes an output amplifier 33. The amplifier 33 may be of conventional design as is commonly used in implantable pacemakers. The design and operation of implantable pacemakers is well known in the art, see, e.g., U.S. Pat. Nos. 4,712,555; 4,817,605; and 5,040,534, incorporated herein by reference. The amplifier 33 delivers a pacing pulse to the heart 14 via the sensing/pacing lead 16 upon receipt of a pacing pulse command signal, referred to herein as a V-pulse 43. (It is to be understood, of course, that use of the term "V-pulse" herein does not necessarily mean that the pacing pulse must be delivered to the ventricle of the heart 14. The pacing pulse may be delivered to the atrium, ventricle, or both chambers of the heart 14 as needed for a particular patient and as permitted by the pacing lead or leads used.)

Still referring to FIG. 1, the sensing channel 30 includes a switch 36, or equivalent circuit element, that selectively connects the sensing/pacing lead 16 to a sense amplifier 38 as controlled by a blocking signal 37, or equivalent. Such blocking is typically done concurrently with and immediately after the delivery of a stimulation pulse, e.g., a V-pulse, to the heart; thereby preventing the input circuits of the sense amplifier from being exposed to the large stimulation pulse. The gain of the sense amplifier is controlled by a gain signal 39. The output of the sense amplifier 38 is directed to one of two inputs of a threshold detector 40, with the other input of the threshold detector being connected to a reference voltage 41. If the output of the sense amplifier exceeds the reference voltage, then the threshold detector output assumes one level (e.g., a high voltage), whereas if the output of the sense amplifier is less than the reference voltage, the threshold detector output assumes another level (e.g., a low voltage).

The blocking signal 37, the gain signal 39, and the reference voltage 41 (used to control the sensing channel 30), and the V-pulse signal (used to control the pacing channel 32), are all generated by control and decision logic 42 as a function of various command signals, timing signals, or other control signals directed to, or generated by, the control and decision logic. The output of the threshold detector 40 is also directed to the control and decision logic 42, and provides such circuitry with an indication as to whether a depolarization signal has been sensed. Advantageously, in accordance with one aspect of the invention, the control and decision logic 42 is configured to adaptively respond to such command, timing, and other control signals, including the output of the threshold detector 40, in order to adjust the blocking signal 37, the gain signal 39 and/or the threshold reference signal 41, to optimally detect a particular type of depolarization signal sensed through the sensing/pacing lead 16.

Timing signals 44, generated by timing circuits 46, are directed to the control and decision logic 42 in order to provide an appropriate time base for determining the rates of sensed depolarization signals and for taking other action in the event no depolarization signals are sensed through the sensing channel. For conventional bradycardia pacing (a function which the ICD 12 can provide), stimulation pulses are generated to pace the heart only if a prescribed time period, referred to generally as the escape interval (EI), elapses without a depolarization signal being sensed. Should a depolarization signal be sensed, then the escape interval is reset. Should the escape interval time-out without a depolarization signal being sensed, a V-pulse command is issued, causing a stimulation pulse to be generated by the output amplifier 33, and the escape interval is reset. In this way, stimulation pulses are provided only "on demand," i.e., as needed by the heart, with the relevant escape interval being reset at the beginning of each cardiac cycle.

Other command signals may be received and relayed to the control and decision logic 42 by way of appropriate telemetry circuitry 48. Telemetry circuitry 48 allows telecommunicative contact to be established with an external programmer device (not shown in FIG. 1). See, e.g., U.S. Pat. No. 4,809,697, for a description of a suitable programming device. See, e.g., U.S. Pat. No. 4,944,299, for a description of appropriate telemetry circuitry. The '697 and '299 patents are incorporated herein by reference. The command signals received through telemetry circuitry 48 may set the operating parameters of the ICD device, such as the basic escape interval used by the timing circuits (which escape interval sets the rate at which stimulation pulses are provided on demand), the initial duration of the refractory period signal 37, the gain signal 39, and/or the reference signal 41, and the like. The telemetry circuitry 48 is also configured to transmit status information and operating data associated with the ICD 12 to be sent to the external programmer. In this way, a cardiologist, or other medical personnel, may noninvasively monitor the operation of the ICD 12 with little or no discomfort to the patient.

The ICD 12 shown in FIG. 1 also includes a cardioversion/defibrillation channel 50 detachably coupled to the electrodes 20 and 22 through the defibrillation leads 24 and 26, respectively. The cardioversion/defibrillation channel 50, like the sensing channel 30 and the pacing channel 32, is controlled and/or monitored by control and decision logic 42. The cardioversion/defibrillation channel 50 includes a charging circuit 50, coupled to a battery 56, and a switching network 54. When the control and decision logic 42 determines that there is a need for a cardioversion or defibrillation pulse, the charging circuit 50 begins building up a sufficiently large electrical charge to effectuate the needed cardioversion or defibrillation pulse. (Note that a cardioversion pulse is typically considered as an electrical stimulation pulse of significantly higher energy than a nominal pacing pulse, and is usually coupled or synchronized to a sensed R-wave; whereas a defibrillation pulse is usually considered as an electrical stimulation pulse that is of even higher energy than a cardioversion pulse. For purposes of the present application, however, the term "defibrillation pulse" will be used to refer generically to any pulse generated by the cardioversion/defibrillation channel 50, regardless of its energy.) Once the needed charge has been stored in the charging circuit 50, the switching network 54 is used to apply the stored charge, i.e., the defibrillation pulse, to the heart 14 through the leads 24 and 26 and the electrodes 20 and 22. Advantageously, the switch network allows the defibrillation pulse to be applied to the heart in accordance with a desired polarity, i.e., the electrode 20 may be positive relative to the electrode 22; or the electrode 22 may be positive relative to the electrode 20.

It should also be noted that some types of cardioversion therapy may be applied to the heart by means of a prescribed sequence of pacing pulses, and/or bursts of pacing pulses, delivered through the pacing channel 32, rather than through the channel 50. See, e.g, U.S. Pat. No. 5,103,822, incorporated herein by reference, which describes one such type of therapy. Once the need for cardioversion therapy has been sensed, i.e., once the control and decision logic determines that the heart is not beating at a proper rate or rhythm, the ICD 12 is typically programmed to first attempt to cardiovert the heart by delivering a prescribed sequence of pacing pulses, or array of pacing pulses at programmed intervals, through the pacing channel 32. If such first attempt fails to restore the heart to a normal cardiac rhythm, then a second attempt will normally include the delivery of one or more low energy defibrillation (cardioversion) pulses through the defibrillation channel 50. If the second attempt fails to restore the heart to a normal cardiac rhythm, then a third attempt will typically include the delivery of one or more high energy defibrillation pulses through the defibrillation channel 50.

As further seen in FIG. 1, the battery 56 within the ICD 12, in addition to providing power to the charging circuit 50, is also used to provide the operating power to the other ICD circuits. Typically, the battery is a 6.4 volt battery, and conventional voltage step-up circuits and regulators are used as required in order to make the requisite operating power available to the ICD circuits.

Figure 2:
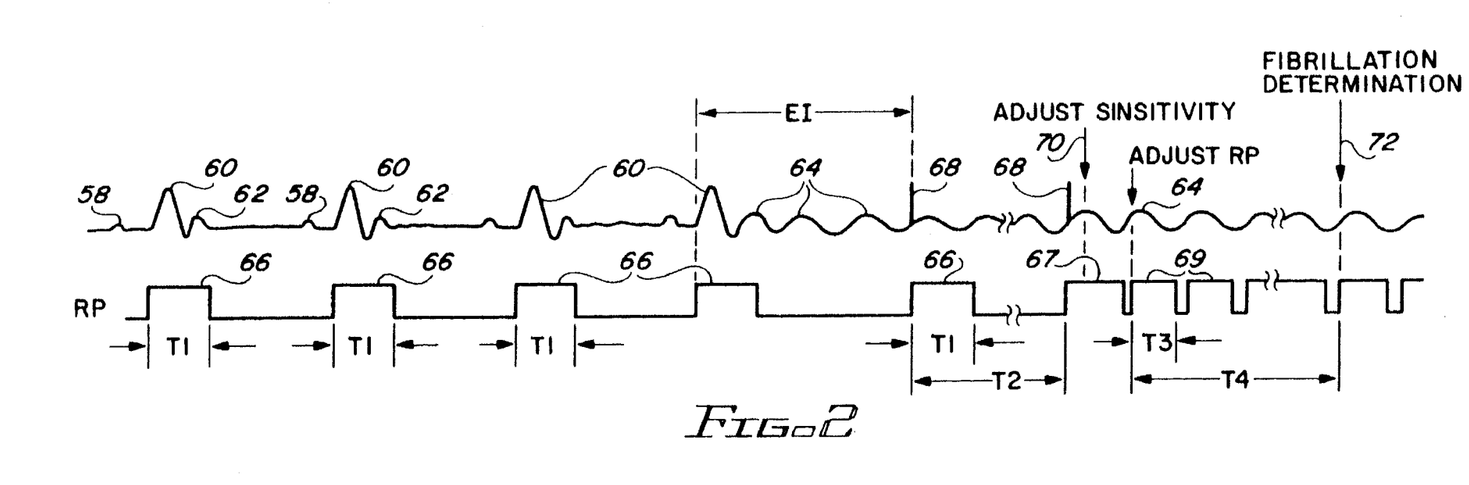
FIGS. 2 and 3 are timing waveform diagrams that illustrate the operation of the ICD of FIG. 1 to determine the presence of a fibrillation condition or a tachycardia condition, respectively.
Figure 3:
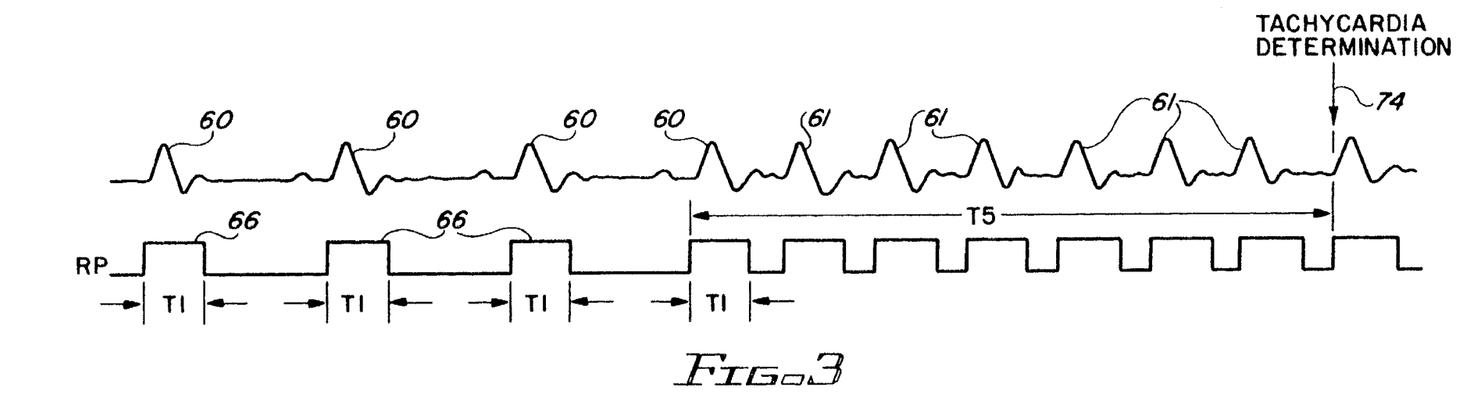

In operation, the ICD 12 senses depolarization signals, e.g., R-waves 60, as depicted in FIGS. 2 and 3. Both FIGS. 2 and 3 show timing waveform diagrams that illustrate the operation of the ICD 12 to determine the presence of a fibrillation condition or a tachycardia condition, respectively. The upper or top waveform in each figure represents the intracardiac electrogram signal sensed at the electrode 18 of the pacing/sensing lead 16. In FIG. 3, such electrogram signal includes a P-wave 58, indicative of the depolarization of the atrium (which is typically sensed through the atrial channel 28), followed by an R-wave 60, sensed through the sensing channel 30 of the ventricular channel, indicative of the depolarization of the ventricle, followed by a T-wave 62, indicative of the repolarization of the ventricle. Such P-R-T-wave sequence represents a normal cardiac cycle that includes an atrial contraction followed by a ventricular contraction, which contractions comprise what is typically referred to as "a heartbeat."

Figure 4:
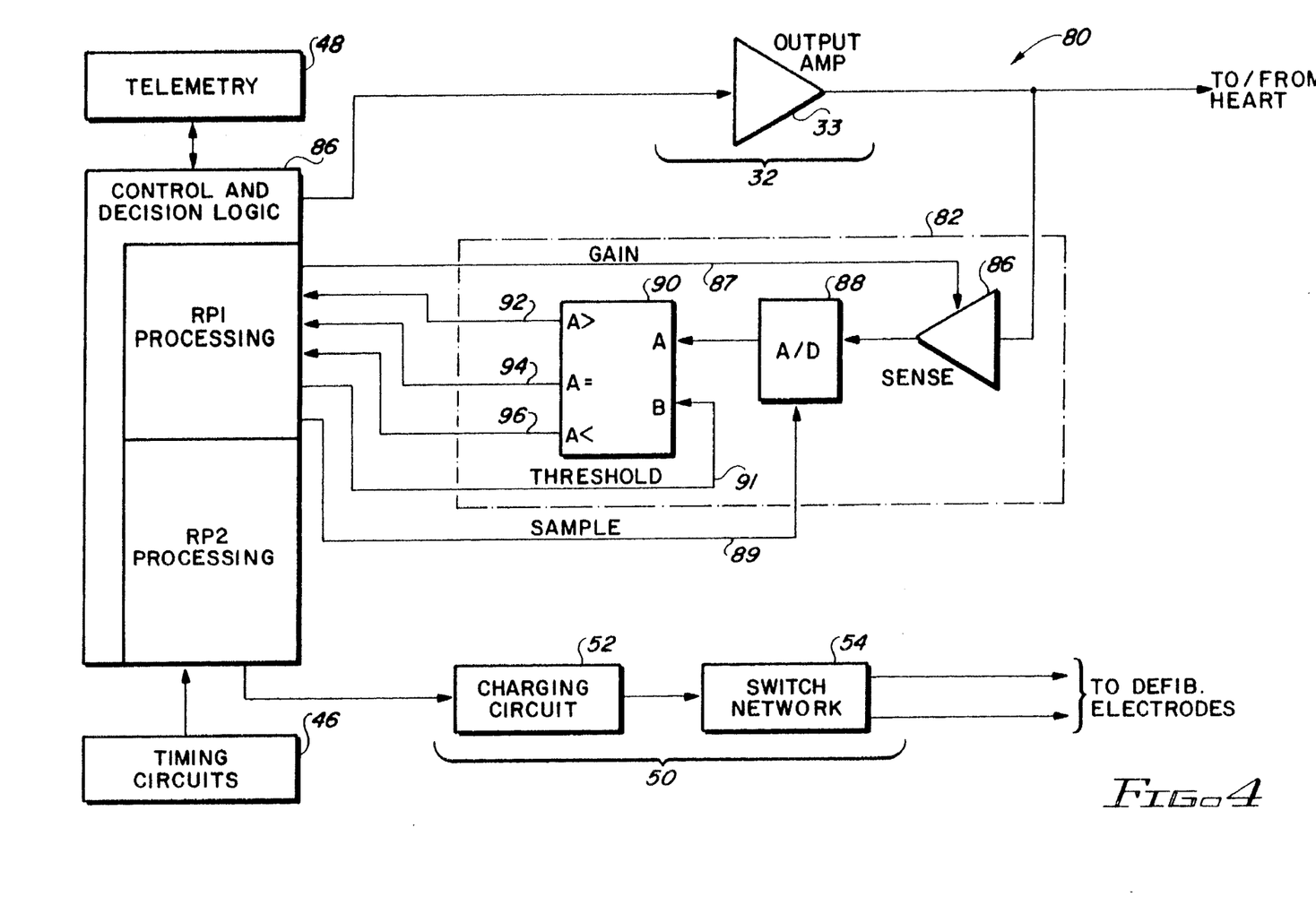
FIG. 4 is block diagram of a preferred embodiment of an ICD made in accordance with the present invention that employs first and second signal processing channels to sense and interpret the depolarization signal.

The sensing channel 30 of the ICD 12 shown in FIG. 1 is adapted to sense an R-wave 60 (FIGS. 3 and 4). An R-wave occurs during depolarization of the ventricle of the heart 14. In response to sensing an R-wave 60, a refractory period (RP) control signal is generated by the control and decision logic 42. The RP control signal thus comprises a pulse train of RP pulses 66, each pulse having a prescribed duration T1, and each pulse being triggered by sensing an R-wave. During the RP pulse 66, the electrogram signal is prevented or blocked from being processed by the control and decision logic 42 (FIG. 1). In addition, during a front portion of the RP pulse 66, the signal from the sensing/pacing lead 16 is actually blocked from being applied to the input of the sense amplifier 38 through use of the switch 36. (In practice, during the time that the RP pulse is present, i.e., during time T1, the control and decision logic 42 of the ICD 12 is made refractory—non-responsive to any input signal.) The duration of the RP pulse 66 is selected to be sufficiently long so as to effectively block or ignore the repolarization T-wave 62, and any other extraneous signals that may be present immediately after the R-wave 60, but sufficiently short so as to allow the next R-wave to be readily detected. Thus, as indicated in FIG. 2, the first four R-waves 60 are sensed by the sensing channel 30, causing the first four RP pulses 66 to be generated.

For the situation represented in FIG. 2, the heart goes into fibrillation immediately after the fourth R-wave 60. Fibrillation is depicted in FIG. 2 as a low amplitude depolarization wave 64 having a frequency that is three-to-five times faster than the normal cardiac rate. It should be understood, however, that while fibrillation is typically characterized by low amplitude depolarization signals, such signals may not occur at a regular rate, but may tend to be chaotic. Whether regular or chaotic, however, the effect is the same as far as the present invention is concerned—the sensing channel 30, having its sensitivity setting (gain 39 and reference 41) set to sense normal R-waves 60, fails to sense any cardiac activity. As a result, after the relevant escape interval has timed-out (which escape interval is represented in FIG. 2 as the time EI), the pacing channel 32 issues a first stimulation pulse 68. The issuance of the stimulation pulse 68 also causes an RP pulse 66 to be generated, just as did the occurrence of an R-wave 60. Thus, an RP pulse 66 follows either the occurrence of an R-wave 60 or the generation of a stimulation pulse 68.

For the fibrillation condition shown in FIG. 2, it is not likely that the stimulation pulse 68 will have any effect on the heart. That is, the stimulation pulse 68 is not of sufficient energy to defibrillate the heart, i.e., to shock the heart back into a normal rhythm. In order to detect the fibrillation condition, the control and decision logic 42 monitors the output of the sensing channel 30 for a prescribed number of stimulation pulses 68, or for a prescribed period of time T2. Upon a failure to detect any output from the sensing channel 30 during the period T2, the control and decision logic 42 automatically adjusts the sensitivity of the sensing channel 30, as indicated at 70 in FIG. 2, so as to better detect the depolarization signals 64 representative of a fibrillating heart. Such adjustment of the sensitivity of the sensing channel is accomplished by increasing the gain of the sense amplifier 38 and/or by lowering the threshold reference of the threshold detector 40. Such adjustment has no effect, however, until the present refractory period, or RP pulse, terminates. Thus, at the conclusion of the particular RP pulse following the adjustment of sensitivity, which RP pulse is pulse 67 in FIG. 2, the sensing channel 30 may be able to sense the depolarization signal 64.

Upon first sensing a depolarization signal after a sensitivity adjustment, the control and decision logic 42, in accordance with one aspect of the invention, also adjusts the refractory period, producing the RP pulse 69. Typically, when looking for a fibrillation condition, the RP pulse, or refractory period, is adjusted to a value T3, where T3>T1. Lengthening the RP pulse effectively masks out some of the chaotic or irregular signals associated with fibrillation, yet still allows a defibrillation signal evidencing fibrillation to be detected.

After a prescribed number of depolarization signals have been detected at the new sensitivity setting, or after a prescribed period of time T4 has elapsed during which the depolarization signals continue to be sensed and/or during which prescribed fibrillation criteria continue to be present (e.g., the continued occurrence of a defibrillation signal having a rate above a certain rate), the control and decision logic 42 makes a determination that a fibrillation condition is present, as depicted at 72 in FIG. 2. Following such determination, the defibrillation channel 50 is activated so that an appropriate response can be made.

The electrogram signal shown in FIG. 3 is similar to the signal shown in FIG. 2, except that after the fourth R-wave 60, the heart breaks into a rapid rhythm, evidenced by closely-spaced R-waves 61, which closely-spaced R-waves occur at a rate that may be two-to-three times faster than the normal cardiac rate. A rapid change to such a fast rate, particularly in the absence of a physiological reason why such rapid rate change should have occurred, is indicative of a tachycardia condition. The R-waves 61 associated with a tachycardia typically remain at an amplitude that allows them to be detected by the sensing channel 30 without further adjustment of the sensitivity setting. Thus, upon sensing the R-waves 60 or the R-waves 61, the RP pulses 66, having a duration of T1, continue to be generated, effectively blocking out the sensing of the repolarization signals (T-waves) or other signals that may occur immediately after the R-wave signals. The control and decision logic 42 monitors the occurrence of such R-waves and applies rate-determining criteria thereto. If the rate of the R-waves exceeds a prescribed threshold, e.g., 170 ppm (pulses per minute), and/or other tachycardia criteria are/is present, and if such condition(s) persist for a prescribed time period T5, or for a prescribed number of R-waves, then a determination is made, at 74, that a tachycardia condition exists. Upon making such determination, appropriate tachycardia treatment is invoked, typically by way of the output channel 33. Such tachycardia treatment may include, for example, the generation of a burst of stimulation pulses, or the generation of a particular pattern of stimulation pulses. See, e.g., U.S. Pat. No. 5,103,822.

Thus, by adaptively adjusting the sensitivity setting and/or the refractory period of the sensing channel 30 in the manner described, the ICD 12 is able to make a determination as to whether a tachycardia condition or a fibrillation condition is present. Once such determination has been made, appropriate therapy can then be evoked in an attempt to terminate such tachycardia or fibrillation condition.

The ICD 12 described above in connection with FIG. 1 may thus be characterized as including: (a) sensing means (30) for sensing intrinsic cardiac depolarization signals of a patient's heart (14) as a function of a sensitivity setting (39, 41); (b) stimulation means (33, 52, 54)) for generating electrical stimulation pulses and delivering such pulses to the patient's heart in accordance with a prescribed stimulation regime; (c) refractory means (36, 37) for generating a first refractory period immediately following the generation of an electrical stimulation pulse by the stimulation means or the sensing of intrinsic cardiac depolarization by the sensing means, with the stimulation means and the sensing means being ineffective during the refractory period; and (d) means (42) for adaptively adjusting the first refractory period of the refractory means and the sensitivity setting of the sensing means to optimally detect whether a given sequence of depolarization signals sensed by the sensing means is indicative of one of a plurality of cardiac conditions.

Turning next to FIG. 4, there is shown a block diagram of a preferred embodiment of an ICD 80 made in accordance with the invention that applies first and second refractory periods to the input signal received through the ventricular channel in order to sense and interpret the depolarization signal. (As required, first and second refractory periods may also be applied to the signal received through the atrial channel.) The ICD 80 includes an output channel 32, having an output amplifier 33; a telemetry circuit 48; timing circuits 46; a charging circuit 50; and a switching network 54 that perform the same function as, and may thus be substantially the same as, the equivalent circuits described above in connection with FIG. 1 The ICD 80 of FIG. 4 also includes control and decision logic 86 that likewise performs the same function as the control and decision logic 42 of FIG. 1, except that it is configured to monitor and control the signal processing channel 82 in accordance with a first refractory period, RP1, or a second refractory period, RP2, as described below.

The input of the signal processing channel 82 is directed to a sense amplifier 86. The gain of the sense amplifier 86 is controlled by a gain signal 87, generated by the control and decision logic 86. The output of the sense amplifier 86 is directed to an analog-to-digital (A/D) converter 88. The A/D converter 88 digitizes the sense amplifier output at a sample time as controlled by a sample signal 89, also generated by the control and decision logic 86. The output of the A/D converter 88, which comprises a digital signal or word, is then directed to a digital threshold detector 90. The detector 90 has two inputs, labeled A and B. The A input receives the digitized signal from A/D converter 88. The B input receives a digital threshold reference signal from the control and decision logic 86. Three outputs are provided from the threshold detector 90. A first output signal 92 indicates if the A input is greater than the B input threshold reference signal. A second output signal 94 indicates if the A input is equal to the B input threshold reference signal. A third output signal 96 indicates if the A input is less than the B input reference signal.

It is noted that the A/D converter 88 and/or the digital threshold detector 90, or their equivalent functions, may actually be carried out within the control and decision logic 86. However, the converter 88 and detector 90 are shown as separate elements apart from the control and decision logic 86 in FIG. 4 for clarity of explanation.

Absent from the signal processing channel 82 is a switch, or similar element, that blocks the input signal from the heart, i.e., the electrogram signal, from being coupled to the sense amplifier 86 during a refractory period. However, it is to be understood that the sense amplifier 86 is protected by way of a "blanking period" during and for a few milliseconds immediately following the delivery of a stimulation pulse by the output amplifier 33 (to protect the input circuits of the sense amplifier 86 from the large stimulation pulse), as is commonly done in all implantable stimulation/sensing devices. The first refractory period applied to the processing channel 82, RP1, as well as the second refractory period applied to the processing channel 82, RP2, is implemented within the control and decision logic 86. Such implementation may take many forms. One implementation, for example, processes the data by sampling the A/D converter 88, as controlled by the sample signal 89, at regular or programmed sampled times. Such sampled data is then processed with the digital threshold detector 90, and then uses such data only after the respective refractory period has elapsed. Thus, after a given sample time, the data output from the digital threshold detector 90 may be further processed by the RP1 processing portion of the control and decision logic 86 only if the first refractory period, RP1, has elapsed. The data output from the digital threshold detector 90 may, in addition, be further processed by the RP2 processing portion of the control and decision logic 86 only if the second refractory period, RP2, has elapsed. In this manner, the control and decision logic 86 operates as though it had two separate signal processing channels; and indeed, for the description that follows, the ICD 80 may be considered as having two separate signal processing channels, more properly characterized as first and second virtual signal processing channels, and referred to as the RP1 virtual processing channel and the RP2 virtual processing channel. The same sense amplifier 86, A/D converter 88, and digital threshold detector 90 may be shared between the RP1 and RP2 virtual processing channels in many instances. As needed, or desired, however, separate sense amplifiers 86 may be employed with each of the RP1 and RP2 virtual processing channels to allow for differing gain settings for each of the virtual processing channels. Likewise, the same sense amplifier 86, and A/D converter 88 may be shared between the RP1 and RP2 virtual processing channels with separate digital threshold detectors 90 employed with each of the RP1 and RP2 channels to allow for differing threshold settings for each of the virtual processing channels.

Figure 5:
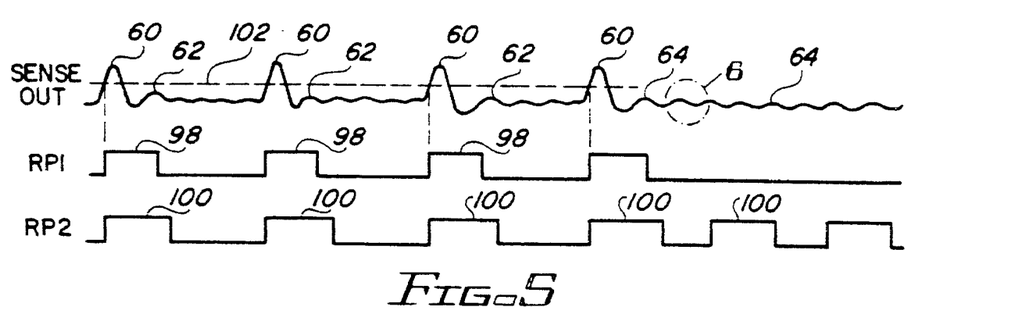
FIG. 5 is a timing waveform diagram that illustrates the operation of the ICD of FIG. 4 as it detects a fibrillation condition.

The operation of the ICD 80 will next be described with reference to the timing waveform diagrams of FIGS. 5–7. FIGS. 4 and 5 illustrate the operation of the ICD 80 as it detects a fibrillation condition, while FIG. 7 illustrates the operation of the ICD 80 as it detects a tachycardia condition. The top waveform in FIG. 5, labeled SENSE OUT, represents the intracardiac electrogram signal after it has been amplified by the sense amplifier 86 associated with the RP1 processing channel. Such waveform includes normal cardiac depolarization signals, e.g. R-waves 60, followed by repolarization T-waves 62.

The first refractory period, RP1, prevents the SENSE OUT signal from being processed within the RP1 processing channel of the control and decision logic 86 during the RP1 pulse 98. Similarly, the second refractory period, RP2, effectively prevents further processing of the SENSE OUT signal within the RP2 signal processing channel during the RP2 pulse 100. However, after the expiration of the RP1 pulse 98, the sample from the A/D converter 88, or equivalent circuit, after being compared to a corresponding reference threshold signal 91 by digital comparator 90, is processed in an appropriate manner by the RP1 processing channel within the control and decision logic 86. During this time, the magnitude of the reference threshold signal 91 relative to the SENSE OUT signal is represented as a dashed line 102 in FIG. 5. It is the digital version of the signal 102 that forms the B input to the digital comparator 90. Similarly, it is the digital version of the SENSE OUT waveform that forms the A input to the digital comparator 90. (It should thus be noted that the dashed line 102 shown in FIG. 5 is useful only for explanation purposes, as the actual threshold signal 91 is a digital signal, as is the SENSE OUT signal after it has been digitized by the A/D converter 88.)

The RP1 pulse 98 is initiated as soon as the digital comparator 90 senses that the digitized SENSE OUT signal exceeds the digitized reference threshold 91 in the RP1 processing channel. Similarly, the RP2 pulse 100 is initiated as soon as the digital comparator 90 senses that the digitized SENSE OUT signal exceeds its corresponding digitized reference threshold signal in the RP2 processing channel. Advantageously, the digitized reference threshold signal for the RP2 processing channel may be set differently than the digitized reference threshold signal for the RP1 processing channel. Similarly, the gain of the sense amplifier 86 when used with the RP2 processing channel may be set differently than when used with the RP1 signal processing channel. In this way, the effective sensitivity settings of the RP1 and RP2 processing channels may be appropriately set for the sensing function of the channel. The RP1 processing channel, for example, should have a sensitivity setting (gain and threshold) aimed at detecting normal magnitude depolarization signals representative of normal cardiac activity or tachycardias. The RP2 processing channel, on the other hand, should have a sensitivity setting aimed at detecting depolarization signals representative of fibrillation, e.g., low amplitude depolarization signals occurring at a fast or chaotic rate.

After the fourth R-wave 60 shown in FIG. 5, a fibrillation condition develops that is manifest by low amplitude depolarization peaks 64 that occur at a rapid rate. (While the rate of such peaks 64 shown in FIG. 5 is represented as a regular rate, it is to be understood that in some instances, the rate may be a chaotic or irregular rate.) Once fibrillation begins, the magnitude of the depolarization peaks 64 is less than the reference threshold 102, and hence the RP1 processing channel ceases to sense any instances of the SENSE OUT signal being greater than the threshold 102. As a result, the RP1 pulse signal is no longer generated. The magnitude of the peaks 64, however, is not so low that the peaks are not sensed by the RP2 processing channel, as depicted in FIG. 6. Note that FIG. 6 shows an exploded view of the SENSE OUT signal for a short period of time after its amplitude drops to a low level.

Figure 6:
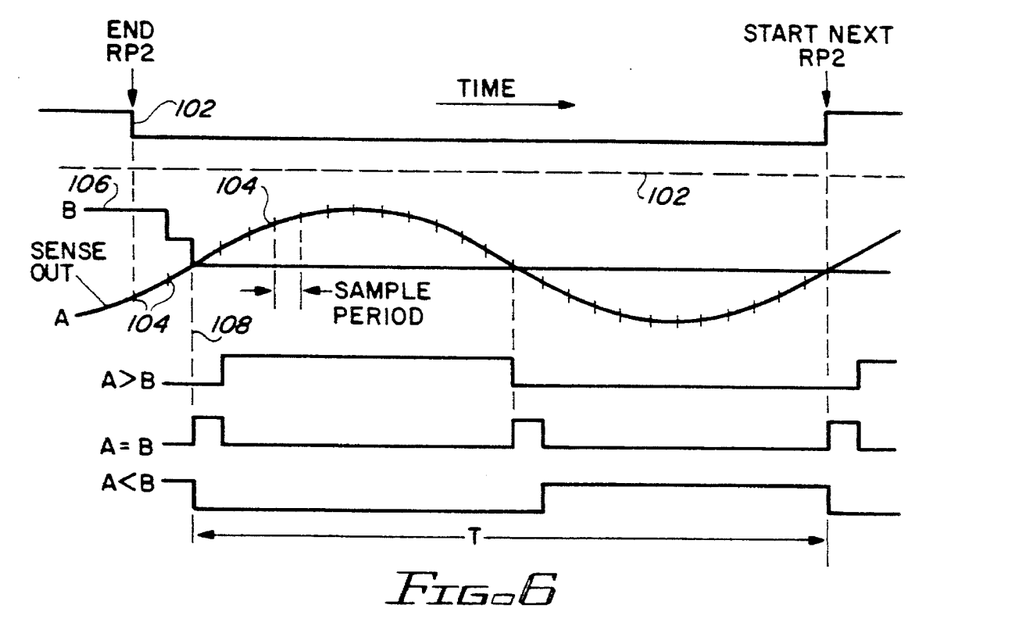
FIG. 6 shows an expanded portion of the depolarization waveform of FIG. 5 and illustrates the operation of the digital comparator circuit of FIG. 4.
Figure 7:
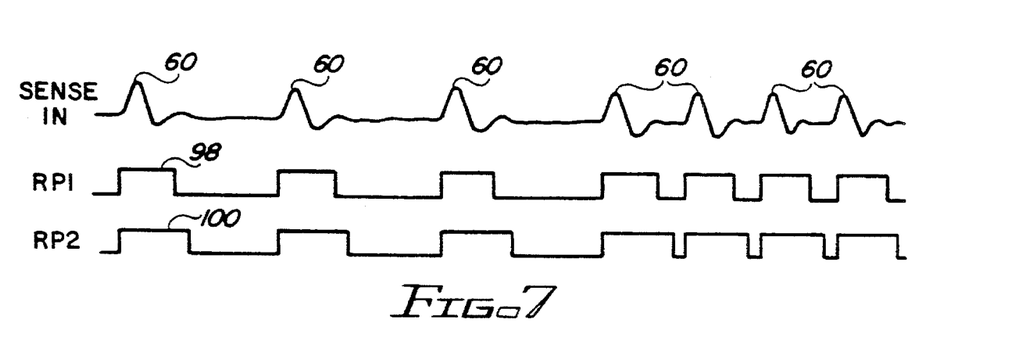
FIG. 7 is a timing waveform diagram that illustrates the operation of the ICD of FIG. 4 as it detects a tachycardia condition.

As illustrated in FIG. 6, as soon as the RP2 pulse ends, at 102, the SENSE OUT signal is sampled at regular sample intervals, indicated by the small tick marks 104. Such sample intervals may be, e.g., every 100–1000 microseconds. At the conclusion of each sample period, the digital comparator 90 of the RP2 channel makes a determination as to whether the A input is greater than, equal to, or less than the B input signal. Further, if the determination is such that the A signal is less than the B signal, i.e., if it is determined that the SENSE OUT signal is less than the reference threshold signal, and if other appropriate criteria are present (such as the SENSE OUT signal is also less than the reference threshold signal determined in the RP1 channel), then the control and decision logic may be programmed to adaptively adjust the B input signal of digital comparator 90 of the RP2 processing channel in accordance with a prescribed adjustment pattern in an attempt to better sense the depolarization signal. Thus, as illustrated in FIG. 6, the B input signal 106 may start out at a high level, but may thereafter be adaptively adjusted downward after each sample time until a point is reached where the A input signal is equal to or greater than the B input signal, as occurs at time 108 in FIG. 6.

Note, as illustrated in FIG. 6, the A>B output signal of the digital comparator 90 of the RP2 channel goes high one sample period after the SENSE OUT signal exceeds the threshold reference signal, and remains high until the SENSE OUT signal is equal to or less than the threshold reference signal. Similarly, the A<B output signal of the digital comparator 90 of the RP2 channel goes high one sample period after the SENSE OUT signal is less than the threshold reference signal, and remains high until the SENSE OUT signal is equal to or grater than the threshold reference signal. The A=B output signal, in contrast, goes high as soon as the SENSE OUT signal is equal to the threshold reference signal as remains high (assuming a waveshape for the SENSE OUT signal as shown in FIG. 6) only for one sample period. (One sample period is equal to the time between two adjacent tick marks 104.) Hence, only one of the three possible output signals of the digital comparator 90 is high at any given time.

The ability to detect a depolarization signal in the RP2 processing channel at the same time that a signal has not been detected in the RP1 processing channel thus provides an indication that a fibrillation condition has occurred. The period T of the A>B or A<B signals may also be monitored to provide a further indication as to the approximate rate of the depolarization signal sensed in the RP2 signal processing channel. The combination of such events (i.e., a signal detected in the RP2 channel, but not in the RP1 channel, plus a rapid or chaotic rate) thus allows the control and decision logic 86 to conclude that a cardioversion or fibrillation condition is present. Once such determination is made, the output channel 32, and/or the defibrillation channel 50 may be activated in order to invoke appropriate cardioversion or defibrillation therapy.

FIG. 7 shows a timing waveform diagram as in FIG. 5, but illustrates a tachycardia condition, e.g., R-waves 60 that occur at a rapid rate. Such R-waves 60 continue to be sensed in both the RP1 and RP2 channels, as evidenced by the continued presence of the RP1 and RP2 pulses 98 and 100. Under such conditions, the control and decision logic can readily determine the rate of the R-waves 60, and if such rate exceeds a predetermined tachycardia rate threshold, then a tachycardia condition is deemed present, whereupon the output channel 32, and/or the defibrillation channel 50, may be activated in order to invoke appropriate antitach therapy.

As described above, it is thus seen that the present invention provides an ICD that utilizes two independently programmable refractory periods, a first refractory period (RP1) being used when sensing normal depolarizations and tachycardias, and a second refractory period (RP2) being used when sensing fibrillation.

Figure 81:
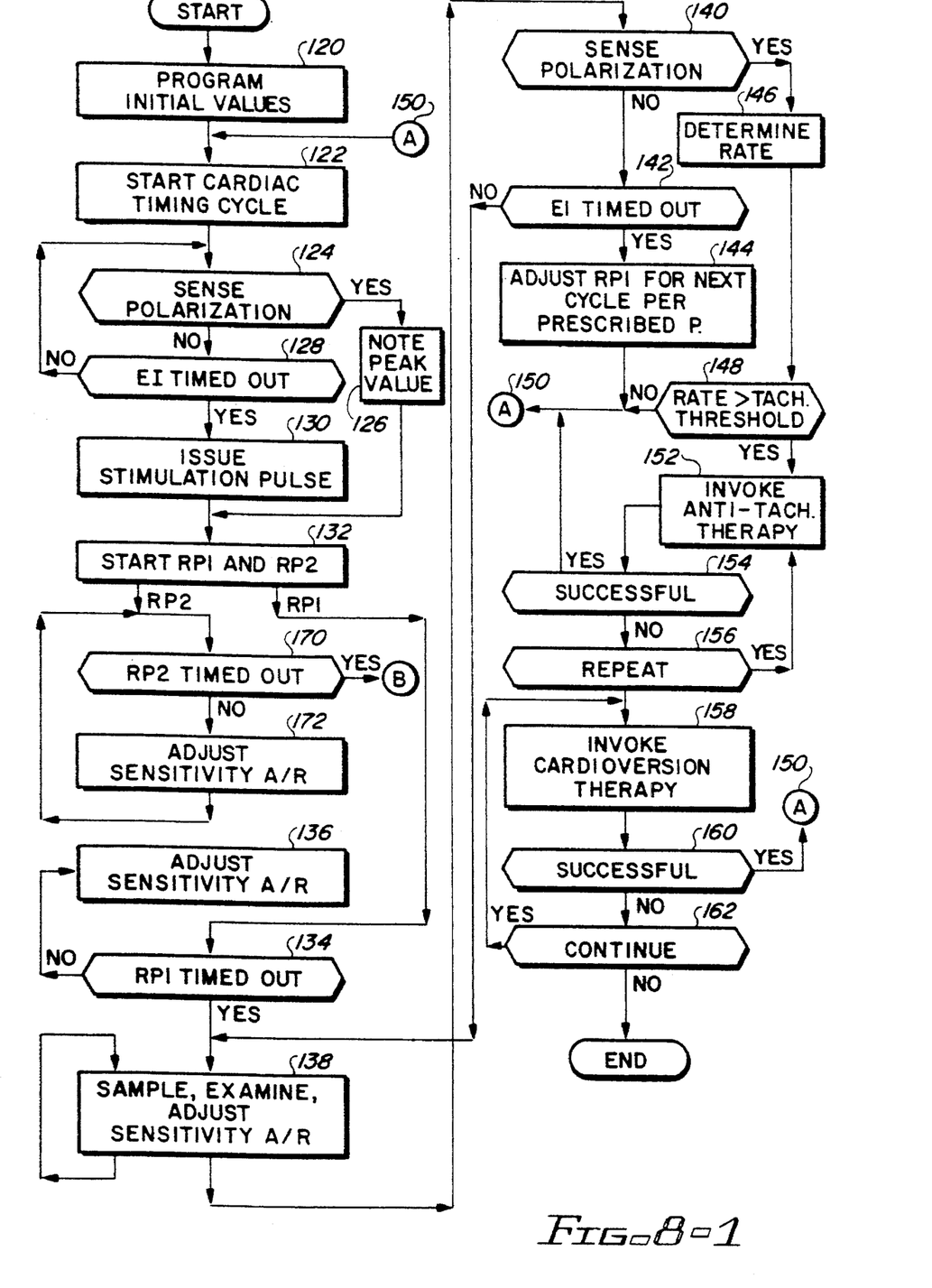
Figure 82:
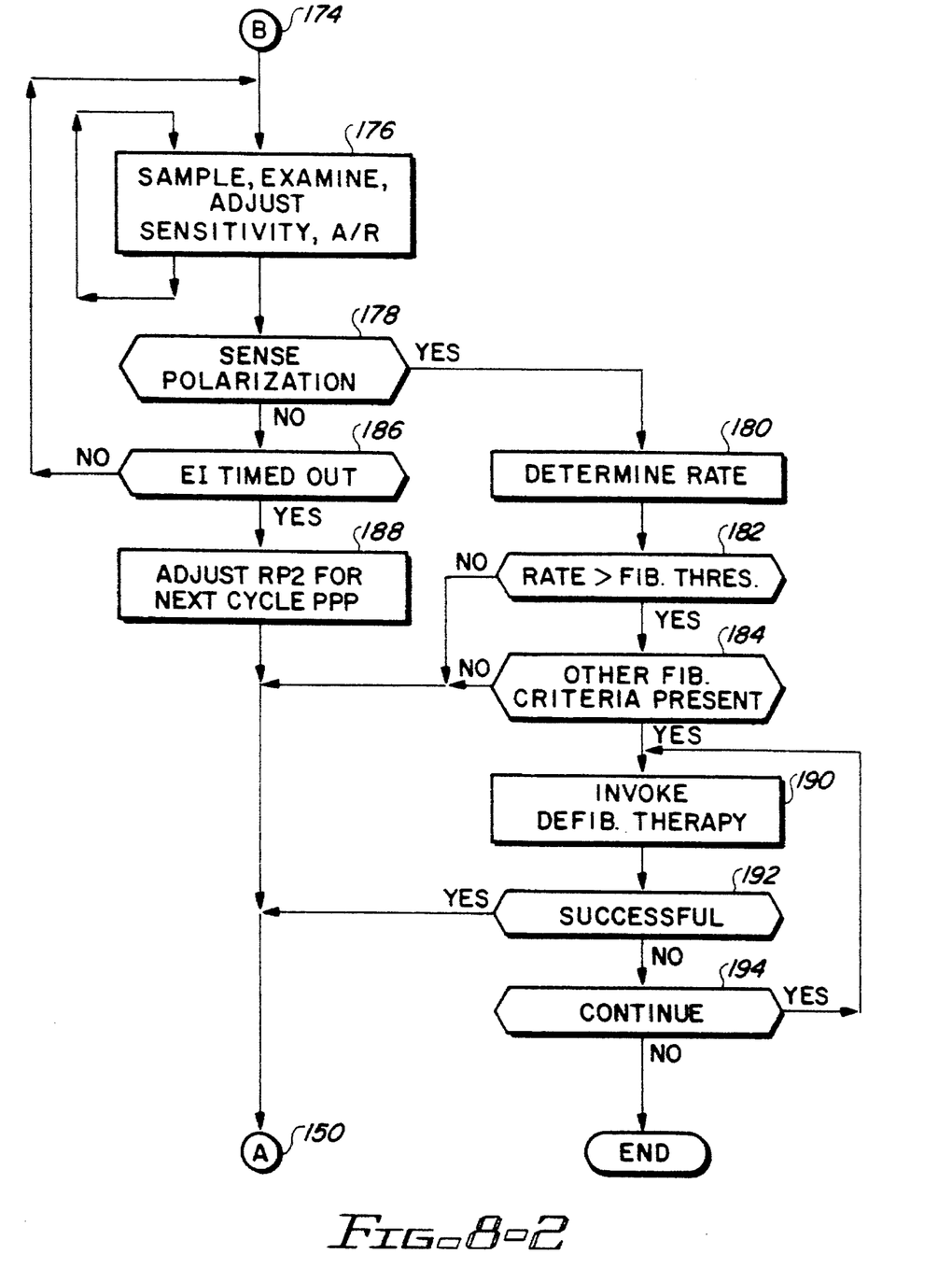

The control and decision logic 86 monitors the output signals from the respective digital comparator circuits 90, or their equivalent, associated with the RP1 and RP2 channels, and controls the operation of the ICD 80, as depicted in the simplified flow chart of FIGS. 8-1 and 8-2. In the preferred embodiment, the control and decision logic 86 is implemented as a microprocessor-based control circuit, or equivalent processor circuit, having appropriate memory associated therewith into which a suitable operating program can be selectively stored. Such processor-based control circuits are well known in the art, as is the manner of programming such circuits in order to have them carry out a desired function. Advantageously, such operating program may be altered, as needed, through the telemetry circuits 48 in conventional manner. Alternatively, the control and decision logic 86 may be implemented using dedicated logic circuitry that is wired to perform the equivalent control provided by a control program.

FIGS. 8-1 and 8-2 depict the basic steps carried out by the operating program, or equivalent control circuit, of the control and decision logic 86. In FIGS. 8-1 and 8-2, each main step or the process is depicted as a "box" or "block," with an appropriate reference number assigned thereto (which is usually referred to in the following discussion parenthetically), and with the interrelationship between each of the main steps of the operating program being indicated by the various lines connecting the various blocks.

Referring to FIG. 8-1, it is seen that once such operating program has been started, the initial values for the control parameters of the program are set (block 120). Such control parameters may include, e.g., the length of RP1 (the refractory period for the RP1 channel), the length of RP2 (the refractory period for the RP2 channel), the length of other time intervals used in the operation of the ICD, such as a basic escape interval (EI), the rate criteria that defines the rate above which a tachycardia or fibrillation condition is presumed present, the initial sensitivity settings of each channel, e.g., the gain and threshold signals, the sample period for use by the A/D converters, and the like. All of these control parameters are set at the factory to nominal values, but most all of them can likewise be programmably changed after the ICD is implanted (to within certain limits) by a physician having access to a suitable programming device.

After the control parameters have been set, a given cardiac cycle begins (block 122). This means that the relevant escape interval, EI, (or equivalent time period), assigned to the ICD is started, which EI defines the longest time period permissible for a cardiac cycle without having the ICD intervene. During the cardiac timing cycle, the output of the RP1 and RP2 channels is monitored to determine if a depolarization signal is sensed (block 124). If so, the peak value of the depolarization signal is noted (block 126), and the two refractory periods, RP1 and RP2, begin (block 132). If not, i.e., if no depolarization is sensed (at block 124) before the timing-out of the escape interval (block 128), then a stimulation pulse is issued by the output amplifier 33. Following issuance of the stimulation pulse, the two refractory periods RP1 and RP2 begin (block 132).

Upon starting the two refractory periods RP1 and RP2, two independent processing routines are followed, as indicated by two separate branches in the flow chart, identified as the RP1 branch, and the RP2 branch. Referring first to the RP1 branch, a determination is made as to whether RP1 has timed-out (block 134). If RP1 has not timed-out, then the sensitivity setting of the RP1 channel (gain and/or threshold) may be adjusted, as required, in anticipation of the sensing function that the RP1 channel will carry out. For example, if a depolarization signal was sensed previously (block 124), the adjustment of the sensitivity carried out at block 136 may include a setting of the threshold reference to a prescribed percent, e.g., 75%, of the peak value (determined at block 126) associated with the previously sensed depolarization signal. Thus, if the sensed depolarization signal had a peak value of 10 millivolts (mV), then the threshold reference used by the RP1 channel would be set to 75% of 10 mV, or 7.5 mV. Other parameters could likewise be adjusted, e.g., the gain of the sense amplifier 86, or even the duration of the RP1 period, as a function of prior sensed events. In this way, the RP1 channel adaptively adjusts its control parameters in order to best detect a particular type of cardiac depolarization event.

Once RP1 has timed-out, the output signal from the sense amplifier 86 is sampled by the A/D converter 86. The sample obtained is examined, and further adjustments to the gain and/or threshold reference level may be made before the next sample time, as required (A/R). Such inter-sample adjustments (made at block 138), if used, are limited to small variations of the inter-cycle adjustments (made at block 136).

If the current sample indicates that the digitized SENSE OUT signal is less than the threshold reference, then that is taken as an indication that a depolarization signal is not present (block 140). In such event, and assuming that the relevant escape interval (EI) that defines the length of the cardiac cycle has not timed-out (block 142), the next sample of the SENSE OUT signal is taken (block 138), and the process repeats (blocks 138, 140). If the EI has timed-out (block 144), and if a depolarization signal has still not been sensed, then the duration of the refractory period for the next cardiac cycle may be adjusted (block 144) in accordance with a prescribed pattern in an attempt to find a depolarization signal that may have been hidden by a refractory period that was perhaps too long. As part of such adjustment (block 144), a stimulation pulse would be issued in an attempt to keep the cardiac rhythm at an appropriate rate.

If the current sample indicates that the digitized SENSE OUT signal is greater than the threshold reference, then that is taken as an indication that a depolarization signal is present. In such instance, the approximate rate of the depolarization signal is determined (block 146). Such rate determination is made by noting the elapsed time since the cardiac cycle began (block 122). An actual rate determination may be made by converting the elapsed time to an appropriate rate (rate $=1/t_p$, where $t_p$ is the elapsed time). Alternatively, the elapsed time can be used directly as an inverse measure of rate.

If the rate determined at block 146 does not exceed a preprogrammed tachycardia rate threshold (block 148), then the operating program returns to block 122 to begin the next cardiac cycle. If, however, the rate determination (made at block 148) does indicate a rate greater than a tachycardia threshold, then a predetermined antitachycardia (antitach) therapy is invoked (block 152), such as that described in U.S. Pat. No. 5,103,822. After invoking such antitach therapy, a determination is made as to whether such therapy was successful (block 154). If successful, the operating program returns to block 122 to begin a new cardiac cycle. If not successful, then a determination is made as to whether such antitach therapy should be invoked again (block 156). Typically, the antitach therapy will be invoked a predetermined (and preferably programmable) number of times, e.g., three times, in an attempt to terminate the tachycardia condition. (As part of making the decision at block 156 to invoke the antitach therapy again, it is understood that a confirmation of the tachycardia condition will first be made). If the antitach therapy is not to be invoked again (block 156), then the operating program next invokes an appropriate cardioversion therapy (block 158). Such therapy may include, for example, the generation and delivery of moderate energy stimulation pulses through the defibrillation channel 50; and/or the delivery of a different burst pattern of pulses through the output channel 32 (see FIG. 4).

Should the cardioversion therapy be successful in terminating the tachycardia (block 160), then the operating program begins a new cardiac cycle by returning to block 122. If not successful, then a determination is made as to whether the cardioversion therapy should be repeated (block 162). Inherent in such determination is a verification that the tachycardia condition responsible for invoking the cardioversion therapy still persists. Typically, such cardioversion therapy is invoked a predetermined (programmable) number of times, e.g., four times. After executing such therapy the predetermined number of times without success, the operating program terminates. Such termination causes the ICD device to revert to a basic operating mode, e.g., VOO pacing. (Sometimes reversion to a basic operating mode will also successfully terminate the detected arrhythmia.)

In parallel with, and substantially independent of, the above processes carried out in the RP1 branch (RP1 channel in FIG. 4) of the flow chart of FIG. 8-1, the operating program is also carrying out certain steps in the RP2 branch (RP2 channel in FIG. 4) of the flow chart as indicated in FIGS. 8-1 and 8-2. The two branches of the flow chart are not totally independent because both are synchronized with the beginning of the cardiac cycle (block 122). However, after the relevant refractory period begins (at block 132), and until such time as the next cardiac cycle is forced to begin, the two branches operate independent of each other.

In most respects, the steps carried out in the RP2 branch are equivalent to the steps carried out in the RP1 branch, described above. That is, the steps carried out at blocks 170, 172, 176, 178, 180, 186 and 188 of the RP2 branch are equivalent to the steps carried out at blocks 134, 136, 138, 140, 146, 142 and 144, respectively, of the RP1 branch, described above. The only difference is that the sensitivity (gain and threshold) of the RP2 branch (RP2 channel) may be completely different than the sensitivity used in the RP1 branch. Further, as the sensitivity of the RP2 branch is adjusted, e.g., at block 172, it is adjusted differently than is the sensitivity of the RP1 branch. For example, the threshold reference value of the RP2 branch may be adjusted (at block 172) to 20% of the peak value determined at block 126. Further, if the duration of the RP2 period is adjusted at block 188, it may be adjusted pursuant to a prescribed pattern (PPP) that is quite different than the prescribed pattern of adjustment followed at block 144 for adjusting RP1. Thus it is seen that the present invention offers a wide variety of adjustment possibilities that make the invention extremely adaptable to best detect the particular depolarization signals of concern.

With reference to FIG. 8-2, it is seen that once the rate of the sensed depolarization signal has been determined (block 180), a determination is made as to whether such rate is greater than a fibrillation threshold rate (block 182). If not, then the next cardiac cycle begins (block 122). If yes, and if other specified fibrillation criteria are present (block 184), such as the failure to sense any depolarization signals in the RP1 channel, then appropriate defibrillation therapy is invoked (block 190). Such defibrillation therapy typically involves delivering the maximum energy defibrillation pulse through the defibrillation channel 50 (FIG. 4). If the defibrillation therapy is not successful, it may be continued a predetermined number of times (blocks 192, 194), providing the need to continue such therapy is verified before repeating the therapy. If it is successful, then the operating program starts a new cardiac cycle (block 122).

As described above, it is thus seen that the invention provides an implantable cardioverter-defibrillator (ICD) (80) that includes: (a) stimulation means (32, 50) for generating electrical stimulation pulses and delivering the pulses to the patient's heart in accordance with a prescribed stimulation regime; and (b) sensing means for sensing intrinsic cardiac depolarization signals of a patient's heart. The sensing means includes first (RP1 channel) and second (RP2 channel) sensing channels having first (RP1) and second (RP2) refractory periods, respectively, that follow a depolarization of the patient's heart and prevent the sensing means from sensing any depolarization signals during the respective refractory period. The RP1 sensing channel is adapted to sense normal depolarizations and tachycardias following the first refractory period (RP1) as a function of a first sensitivity setting. The RP2 sensing channel is adapted to sense fibrillation following the second refractory period (RP2) as a function of a second sensitivity setting. Control means (86) are also included within the ICD (80) for defining the first and second refractory periods, the first and second sensitivity settings and the prescribed stimulation regime.

It is also seen that the ICD provided by the invention adaptively adjusts the gain and/or threshold settings of the respective signal processing channels to optimally sense the relatively high magnitude depolarization signals associated with normal cardiac depolarizations and tachycardias, or the relatively low magnitude depolarization signals associated with fibrillation.

As further evident from the above description, the ICD provided by the invention provides two parallel signal processing channels that respond to the depolarization signals sensed over a single sensing lead (or lead network). Each processing channel has its own independently programmable refractory period associated therewith, and each signal processing channel further has its own independently adjustable gain and/or threshold setting associated therewith.

The present invention also includes, as likewise seen from the above description, a method of distinguishing normal cardiac activity, including a tachycardia, from cardiac fibrillation. Such method includes eight steps. First, depolarization signals are electrically sensed. Second, the depolarization signals sensed in first step are simultaneously processed in first (RP1) and second (RP2) signal processing channels. Third, the RP1 signal processing channel is made refractory during a first refractory period (RP1) that begins at the beginning of a cardiac cycle. (The cardiac cycle begins following a sensed or paced depolarization.) The duration of the first refractory period is selected to prevent sensing the afterpotential and repolarization signals associated with a paced or natural depolarization. Fourth, a first sensitivity setting is applied to the RP1 signal processing channel. The first sensitivity setting is selected to sense depolarization signals representative of normal depolarization and tachycardia. Fifth, a depolarization signal sensed in the RP1 signal processing channel is deemed indicative of normal cardiac rhythm if sensed subsequent to the termination of the first refractory period and prior to the beginning of the next cardiac cycle when the sensed depolarization signal conforms to normal depolarization criteria (such as a normal rate). In contrast, a depolarization signal sensed in the RP1 signal processing channel is deemed indicative of a tachycardia condition if sensed subsequent to the termination of the first refractory period and prior to the beginning of the next cardiac cycle when providing the sensed depolarization signal conforms to tachycardia criteria (such as a fast rate). Sixth, the RP2 signal processing channel is made refractory during a second refractory period (RP2) that begins at the beginning of the cardiac cycle. The duration of the second refractory period is selected to prevent falsely identifying the paced event afterpotential as a second intrinsic depolarization. Seventh, a second sensitivity setting is applied to the RP2 processing channel. Such second sensitivity setting is adjusted to sense depolarization signals representative of fibrillation. Eighth, the presence of fibrillation is recognized if a depolarization signal is sensed by the RP2 processing channel subsequent to the termination of the second refractory period and before the beginning of the next cardiac cycle when the sensed depolarization signal conforms to prescribed fibrillation criteria.

The present invention also includes a method of treating tachycardia and fibrillation with an implantable cardioverter-defibrillator (ICD) device (80). As a first step of such method, cardiac depolarization signals are sensed in a first signal processing channel (RP1 channel) within the ICD device. Such first signal processing channel has a first refractory period (RP1) and a sensitivity setting (gain and threshold) selected to sense cardiac depolarization signals representative of normal cardiac depolarization, including depolarization associated with tachycardia. As a second step of the method, the rate of the cardiac depolarization signals is sensed in the first signal processing channel. Based on the rate determined, a determination is made as to whether such depolarization signals are representative of a normal cardiac rhythm or a tachycardia rhythm. As a third step, the method applies a prescribed antitachycardia therapy through the ICD device in response to determining that a tachycardia rhythm is present. As a fourth step, cardiac depolarization signals are sensed in a second signal processing channel (RP2 channel) within the ICD. The second signal processing channel has a second refractory period (RP2) and a sensitivity setting (gain and threshold) selected to sense cardiac depolarization signals representative of fibrillation. As a fifth step, a determination is made as to whether the cardiac depolarization signals sensed in the second signal processing channel, in combination with other prescribed criteria, are representative of fibrillation. As a sixth step, a prescribed fibrillation therapy is applied through the ICD device in response to determining that fibrillation is present.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter-defibrillator (ICD) comprising:

sensing means for sensing intrinsic cardiac depolarization signals of a patient's heart as a function of a first sensitivity setting;

stimulation means for generating electrical stimulation pulses and delivering said pulses to the patient's heart in accordance with a prescribed stimulation regime;

refractory means for generating a first refractory period immediately following the generation of an electrical stimulation pulse by said stimulation means or the sensing of intrinsic cardiac depolarization by said sensing means, whichever occurs first, said stimulation means and said sensing means being inhibited during said refractory period; and means for adaptively adjusting the first refractory period of said refractory means and the first sensitivity setting of said sensing means to optimally detect whether a given sequence of depolarization signals sensed by said sensing means is indicative of one of a plurality of cardiac conditions.

2. The ICD, as set forth in claim 1, wherein said means for adaptively adjusting the first sensitivity setting adjusts the sensitivity setting to a second sensitivity setting that is more sensitive to lower amplitude depolarization signals than said first sensitivity setting.

3. The ICD, as set forth in claim 2, wherein said means for adaptively adjusting the refractory period adjusts the first refractory period to a second refractory period that is longer than said first refractory period.

4. The ICD, as set forth in claim 3, wherein the sensing of depolarization signals above a first prescribed rate when using said second refractory period and when using said second sensitivity setting provides an indication of a fibrillation condition, said prescribed stimulation regime of said stimulation means including a specified defibrillation therapy in response to such indication of a fibrillation condition.

5. The ICD, as set forth in claim 1, wherein the sensing of depolarization signals having a rate above a second prescribed rate and when using said first sensitivity setting provides an indication of a tachycardia condition, said prescribed stimulation regime of said stimulation means including a specified antitachycardia therapy in response to such indication of a tachycardia condition.

6. An implantable cardioverter-defibrillator (ICD) comprising:

stimulation means for generating electrical stimulation pulses and delivering said pulses to a patient's heart in accordance with a prescribed stimulation regime;

sensing means for sensing intrinsic cardiac depolarization signals of the patient's heart, said sensing means including first and second sensing channels having first and second refractory periods, respectively, said first and second refractory periods each beginning following a depolarization of the patient's heart, said first and second sensing channels being prevented from sensing any depolarization signals during their respective refractory periods, said first sensing channel being adapted to sense normal depolarizations and tachycardias following said first refractory period as a function of a first sensitivity setting, and said second sensing channel being adapted to sense fibrillation following said second refractory period as a function of a second sensitivity setting; and control means for defining said first and second refractory periods, said first and second sensitivity settings and said prescribed stimulation regime.

7. The ICD, as set forth in claim 6, wherein said stimulation means includes means for generating and delivering a first type of electrical stimulus aimed at tachycardia termination, and a second type of electrical stimulus aimed at defibrillation.

8. The ICD, as set forth in claim 6, wherein each of said sensing channels includes:

an input amplifier that receives and amplifies depolarization signals as controlled by a gain control signal; and threshold means that compares the depolarization signal amplified by said input amplifier to a reference threshold signal, and provides an output signal only when a prescribed relationship exists between said amplified depolarization signal and said reference threshold signal, said gain control signal and reference threshold signal comprising the sensitivity setting for the sensing channel.

9. The ICD, as set forth in claim 8, wherein said reference threshold signal comprises a digital signal, and wherein said threshold means includes:

an analog-to-digital (A/D) converter coupled to the output of said input amplifier that converts the amplified depolarization signal to a digital signal; and a digital comparator circuit that compares the output of said A/D converter to digital reference signal.

10. The ICD, as set forth in claim 9, wherein said digital comparator circuit generates one of three possible output signals at a given sample time depending upon whether the output of the A/D converter is greater than, equal to, or less than, respectively, the digital reference signal at the particular sample time when the comparison is made.

11. The ICD, as set forth in claim 9, wherein said control means includes means for adaptively adjusting said sensitivity setting of each sensing channel pursuant to a prescribed pattern during a given cardiac cycle.

12. The ICD, as set forth in claim 9, wherein said control means includes means for adjusting the refractory period of a selected one of said sensing channels pursuant to a prescribed adjustment pattern.

13. An implantable cardioverter-defibrillator (ICD) comprising:

sensing means for sensing intrinsic cardiac depolarization signals of a patient's heart;

stimulation means responsive to said sensing means for generating electrical stimulation pulses and delivering said pulses to the patient's heart in accordance with a prescribed stimulation regime;

said sensing means including a refractory period that follows a depolarization of the patient's heart, said refractory period being divided into segments, with a different sensing option being activated at the conclusion of each segment to optimally sense a prescribed type of cardiac activity.

14. The ICD, as set forth in claim 13, wherein a first sensing option, activated at the conclusion of a first segment of said refractory period, includes a sensitivity setting aimed at sensing normal depolarizations and tachycardias, and a second sensing option, activated at the conclusion of a second segment of said refractory period, includes a sensitivity setting aimed at sensing fibrillation.

15. The ICD, as set forth in claim 14, further comprising a control means for adaptively adjusting the duration of said refractory period, including the duration of the respective segments used therein.

16. A method of distinguishing normal cardiac activity, including a tachycardia, from cardiac fibrillation comprising the steps of:

(a) electrically sensing depolarization signals;

(b) simultaneously processing the depolarization signals sensed in step (a) in first and second signal processing channels;

(c) making the first signal processing channel refractory during a first refractory period that begins at the beginning of a cardiac cycle, said cardiac cycle beginning following a sensed or paced depolarization, the duration of said first refractory period being selected to prevent sensing of the afterpotential and repolarization;

(d) applying a first sensitivity setting to the first signal processing channel that is adapted to sense depolarization signals representative of normal depolarization and tachycardia;

(e) recognizing the presence of a normal depolarization if a depolarization signal is sensed by said first signal processing channel subsequent to the termination of said first refractory period and prior to the beginning of the next cardiac cycle when the sensed depolarization signal conforms to normal depolarization criteria, and recognizing the presence of a tachycardia if a depolarization signal is sensed by said first signal processing channel subsequent to the termination of said first refractory period and prior to the beginning of the next cardiac cycle when the sensed depolarization signal conforms to tachycardia criteria;

(f) making the second signal processing channel refractory during a second refractory period that begins at the beginning of said cardiac cycle, the duration of said second refractory period being selected to prevent falsely identifying the paced event afterpotential as a second intrinsic depolarization;

(g) applying a second sensitivity setting to the second signal processing channel that is adapted to sense depolarization signals representative of fibrillation; and (h) recognizing the presence of fibrillation if a depolarization signal is sensed by said second signal processing channel subsequent to the termination of said second refractory period and before the beginning of the next cardiac cycle when the sensed depolarization signal conforms to prescribed fibrillation criteria.

17. The method, as set forth in claim 16, wherein the sensitivity setting of each of said first and second signal processing channels includes a gain setting and a threshold setting, and further including detecting the peak value of a sensed depolarization signal at the beginning of a cardiac cycle, and adaptively adjusting the threshold setting of each of said first and second signal processing channels to be a prescribed percent of the peak value previously sensed.

18. The method, as set forth in claim 17, wherein the prescribed fibrillation criteria used in step (h) comprises the absence of sensed depolarization signals in said first signal processing channel and a rate associated with the depolarization signals sensed in said second signal processing channel that exceeds a prescribed fibrillation threshold.

19. The method, as set forth in claim 17, further including adaptively adjusting the duration of said first refractory period for the next cardiac cycle in the event a depolarization signal is not sensed before the beginning of the next cardiac cycle.

20. The method, as set forth in claim 17, further including adaptively adjusting the duration of said second refractory period for the next cardiac cycle in the event a depolarization signal is not sensed before the beginning of the next cardiac cycle.

21. A method of treating tachycardia and fibrillation with an implantable cardioverter-defibrillator (ICD) device comprising:

(a) sensing cardiac depolarization signals in a first signal processing channel within said ICD device, said first signal processing channel having a first refractory period and a sensitivity setting adapted to sense cardiac depolarization signals representative of normal cardiac depolarization, including depolarization associated with tachycardia;

(b) determining the rate of the cardiac depolarization signals sensed in the first signal processing channel and determining whether such depolarization signals are representative of a normal cardiac rhythm or a tachycardia rhythm;

(c) applying a prescribed antitachycardia therapy through said ICD device in response to determining that a tachycardia rhythm is present;

(d) sensing cardiac depolarization signals in a second signal processing channel within said ICD, said second signal processing channel having a second refractory period and a sensitivity setting adapted to sense cardiac depolarization signals representative of fibrillation;

(e) determining whether the cardiac depolarization signals sensed in the second signal processing channel, in combination with other prescribed criteria, are representative of fibrillation; and (f) applying a prescribed fibrillation therapy through said ICD device in response to determining that a fibrillation is present.

22. The method, as set forth in claim 21, wherein the other prescribed criteria include the absence of a sensed depolarization signal in said first signal processing channel and a rate associated with the depolarization signals sensed in the second signal processing channel that is greater than a prescribed fibrillation threshold.

* * * * *